US 8,494,791 B2

(12) United States Patent
Hazard et al.

(10) Patent No.: US 8,494,791 B2
(45) Date of Patent: Jul. 23, 2013

(54) METHODS AND SYSTEMS FOR IMPROVED CORRELATION OF SHEAR DISPLACEMENT WAVEFORMS

(75) Inventors: Christopher Robert Hazard, Niskayuna, NY (US); Kenneth Wayne Rigby, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 201 days.

(21) Appl. No.: 12/970,676

(22) Filed: Dec. 16, 2010

(65) Prior Publication Data

US 2012/0158323 A1    Jun. 21, 2012

(51) Int. Cl.
| G01F 17/00 | (2006.01) |
| A61B 8/00 | (2006.01) |
| G06K 9/00 | (2006.01) |
| G01N 9/24 | (2006.01) |

(52) U.S. Cl.
USPC ............... 702/56; 600/443; 382/131; 73/602

(58) Field of Classification Search
USPC .................. 702/56–57, 66–67, 70–73, 75–76, 702/81, 84, 94–95, 103, 106, 127, 150, 159, 702/166, 168, 170–172, 189–190; 382/103, 382/107, 128, 131, 190–191, 195, 203, 207, 382/216; 73/584, 597, 602–604, 618, 620–621, 73/627, 629, 632–633, 642, 645–646; 600/407, 600/437–438, 443, 448, 587
See application file for complete search history.

(56) References Cited

U.S. PATENT DOCUMENTS

| 5,606,971 A | 3/1997 | Sarvazyan |
| 7,252,004 B2 | 8/2007 | Fink et al. |
| 7,374,538 B2 * | 5/2008 | Nightingale et al. ......... 600/443 |
| 2008/0249408 A1 | 10/2008 | Palmeri et al. |

FOREIGN PATENT DOCUMENTS

WO    0180742 A1    11/2001

OTHER PUBLICATIONS

M. L. Greenberg et al; "Shear-Wave Velocity Estimation in Porous Rocks: Theoretical Formulation, Preliminary Verification and Applications"; Atlantic Richfield Corp., Plano, TX, U.S.A. Arco Oil and Gas Company, Houston, TX, U.S.A; Article first published online: Apr. 27, 2006; DOI: 10.1111/j.1365-2478.1992.tb00371.x; vol. 40, Issue 2; Abstract-1 Page.
Edwin L. Carstensen et al; "Elastography in the Management of Liver Disease"; doi:10.1016/j. ultrasmedbio.2008.03.2002; pp. 1535-1546.

* cited by examiner

*Primary Examiner* — Toan Le
(74) *Attorney, Agent, or Firm* — Scott J. Asmus (57) ABSTRACT

Methods and systems for improving correlation of shear displacement waveforms are presented. The method includes delivering one or more reference pulses to a plurality of target regions to detect corresponding initial positions. Further, a plurality of pushing pulse segments are delivered to one or more pushing locations, where one or more parameters corresponding to the plurality of pushing pulse segments are adapted for generating a shear displacement waveform with a desired wave shape. Additionally, one or more tracking pulses may be delivered to the plurality of target regions for detecting displacements of at least a subset of the target regions as a function of time. Particularly, the displacements are determined as time samples of the shear displacement waveform. Subsequently, a shift between the shear displacement waveform detected at least two different target regions in the subset of the plurality of target regions is detected.

19 Claims, 4 Drawing Sheets

METHODS AND SYSTEMS FOR IMPROVED CORRELATION OF SHEAR DISPLACEMENT WAVEFORMS

STATEMENT OF GOVERNMENT INTEREST

This invention was made with government support under R01 AG029804 awarded by National Institutes of Health. The government has certain rights in the invention.

BACKGROUND

Embodiments of the disclosure relate to ultrasound imaging, and more particularly to shear wave elasticity imaging with improved shear wave velocity estimation.

Medical diagnostic ultrasound is an imaging modality that employs ultrasound waves to probe the acoustic properties of biological tissues and produce a corresponding image. Particularly, diagnostic ultrasound systems are used to visualize muscles, tendons, and many internal organs to capture their size, structure and any pathological lesions using near real-time tomographic images. Further, diagnostic ultrasound also finds use in therapeutic procedures where an ultrasound probe is used to guide interventional procedures such as biopsies.

Generation of ultrasound pulses and detection of the reflected energy is typically accomplished via a plurality of transducers located in the ultrasound probe in proximity or contact with a patient. Such transducers typically include electromechanical elements capable of converting electrical energy into mechanical energy for transmission and mechanical energy back into electrical signals on reception. These electrical signals are further processed and transformed into a digital image of the target region, such as biological tissues.

Recent ultrasound imaging techniques employ acoustically generated shear waves to determine the mechanical properties of biological tissues. Particularly, some of these techniques track shear wave induced displacements through a region of interest to determine tissue mechanical properties such as shear speed and shear elastic modulus. Shear waves are generated in a phantom or target tissues by delivering one or more pushing pulses to a target region. The pushing pulses typically have higher amplitudes and longer lengths than the acoustic pulses employed in B-mode or Color Doppler ultrasound imaging. Accordingly, the pushing pulses generate shear waves that travel from the point of generation through the tissue causing time varying displacements at multiple locations along the tissue. Further, the displacements caused by the shear wave may be detected using standard Doppler tracking pulses. Tracking the shear wave induced displacements as a function of time at the multiple locations allows an estimation of shear velocity, which in turn, is related to one or more mechanical properties of the tissue.

Characterization of tissue mechanical properties such as shear stiffness using shear velocity estimation has important medical applications as these properties are closely linked to tissue state with respect to pathology. Typically, at least a portion of a tissue may become stiffer than surrounding tissues indicating an onset or presence of a disease such as cancer, tumor, fibrosis, steatosis or other such conditions. Conventional shear velocity estimation techniques, however, suffer from inherently low signal-to-noise ratio (SNR) resulting in inefficient shear wave tracking, which may further result in erroneous velocity and stiffness computations. The erroneous stiffness values, in turn, may affect the accuracy of a medical diagnosis. Attempts to improve the SNR by increasing the amplitude and/or duration of the pulses used to create the shear waves may lead to increased acoustic radiation dosage for clinical use, and therefore may be unfeasible.

It is, thus, desirable to develop effective methods and systems for efficient shear wave elasticity imaging. Particularly, there is a need for methods and systems that, for example, improve the shear wave velocity estimation, frame rates and spatial resolution while optimizing the ultrasound radiation dosage.

BRIEF DESCRIPTION

In accordance with aspects of the present technique, a method for improving correlation of shear displacement waveforms is presented. The method includes delivering one or more reference pulses to a plurality of target regions to detect initial positions of the plurality of target regions. Further, a plurality of pushing pulse segments are delivered to one or more pushing locations. Particularly, one or more parameters corresponding to the plurality of pushing pulse segments are adapted for generating at least one shear displacement waveform with a desired wave shape. Further, one or more tracking pulses are delivered to the plurality of target regions for detecting displacements of at least a subset of the plurality of target regions as a function of time. Particularly, the displacements are determined as time samples of the shear displacement waveform. Subsequently, a shift between the shear displacement waveform detected at least two different target regions in the subset of the plurality of target regions is determined.

In accordance with aspects of the present system, an ultrasound imaging system is presented. The system includes a transducer array that delivers a plurality of pulses to a plurality of target regions. To that end, the plurality of pulses include one or more reference pulses, one or more tracking pulses delivered to the plurality of target regions and at least one pushing pulse delivered to one or more pushing locations as a plurality of pushing pulse segments. The system further includes a pulse shaping unit communicatively coupled to the transducer array. The pulse shaping unit generates at least one shear displacement waveform with a desired wave shape using one or more adapted parameters corresponding to the plurality of pushing pulse segments. Additionally, the system also includes a processing unit communicatively coupled to at least one of the pulse shaping unit and the transducer array. The processing unit adapts the one or more parameters corresponding to the plurality of pushing pulse segments to enable the pulse shaping unit to generate the shear displacement waveform with the desired wave shape. Further, the processing unit processes data received from at least a subset of the plurality of target regions in response to the plurality of pushing pulse segments to determine displacements of the plurality of target regions, where the displacements are time samples of the shear displacement waveform. Subsequently, the processing unit determines a shift between the shear displacement waveform detected at least two different target regions in the subset of the plurality of target regions.

In accordance with another aspect of the present technique, a non-transitory computer readable storage medium with an executable program thereon for improving correlation of shear displacement waveforms is disclosed. Particularly, the executable program instructs a processing unit to deliver one or more reference pulses to a plurality of target regions to detect corresponding initial positions. Further, a plurality of pushing pulse segments are delivered to one or more pushing locations under program instruction. To that end, one or more parameters corresponding to the plurality of pushing pulse segments are adapted for generating at least one shear displacement waveform with a desired wave shape. Additionally, one or more tracking pulses are delivered to the one or more target regions for detecting displacements of at least a subset of the plurality of target regions as a function of time. Particularly, the displacements are determined as time samples of the shear displacement waveform. Subsequently, the program instructs a processing unit to determine a shift between the shear displacement waveform detected at least two different target regions in the subset of the plurality of target regions.

DRAWINGS

These and other features, aspects, and advantages of the present technique will become better understood when the following detailed description is read with reference to the accompanying drawings in which like characters represent like parts throughout the drawings, wherein.

DETAILED DESCRIPTION

The following description presents systems and methods for enhanced shear wave elasticity imaging (SWEI). Particularly, certain embodiments illustrated herein describe the systems and the methods that greatly improve the correlation of shear displacement waveforms, and thus, the estimation of mechanical characteristics such as shear stiffness while imaging a target object such as biological tissues. Although the following description includes only a few embodiments, the SWEI systems and methods may be implemented in various other imaging systems and applications to achieve enhanced imaging with optimized processing and dose control. By way of example, the SWEI systems and methods may also be used for monitoring target drug and gene delivery and nondestructive testing of elastic materials such as plastics and aerospace composites that may be suitable for ultrasound imaging. The systems and methods described in the present disclosure also find use in detecting cancerous lesions in breast, thyroid, liver, or other organs. Additionally, the present systems and methods may also be used to help diagnosis and stage liver fibrosis, and to help monitor therapies including, high-intensity focused ultrasound (HIFU), radiofrequency ablation (RFA), and brachytherapy. An exemplary environment that is suitable for practicing various implementations of the present system is described in the following sections with reference to FIG. 1.

Figure 1:
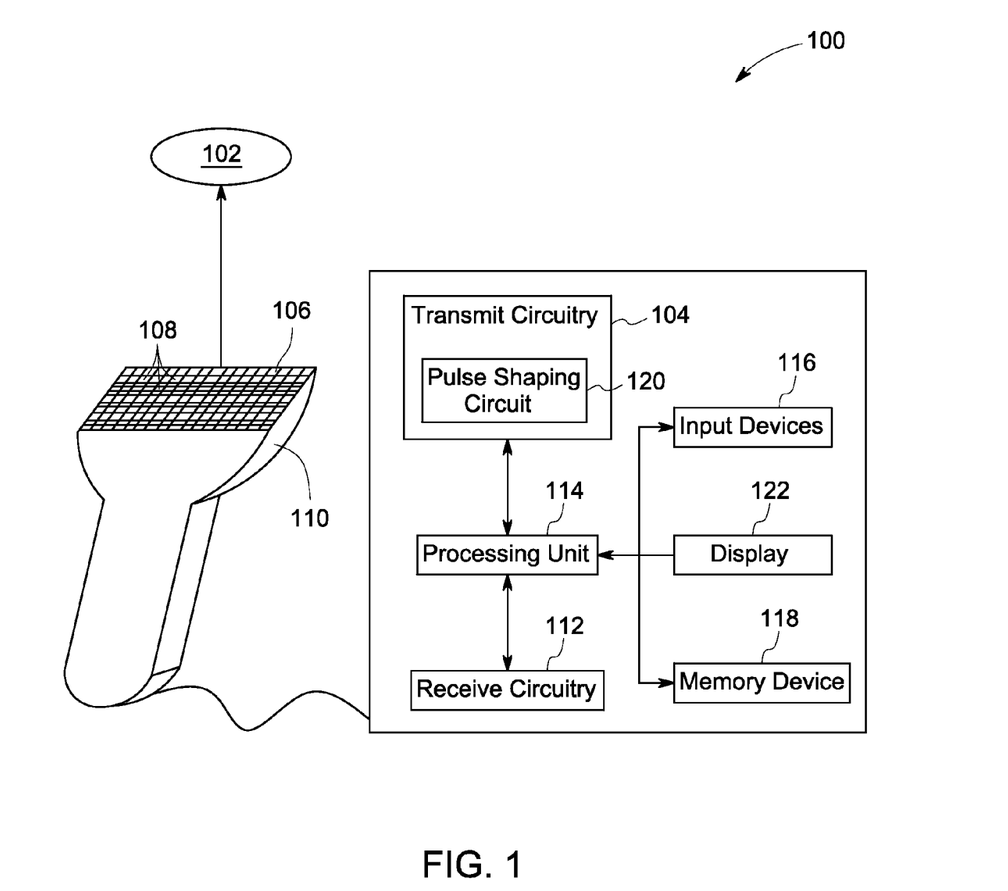
FIG. 1 is a schematic representation of an exemplary shear wave elasticity imaging system, in accordance with aspects of the present system.

FIG. 1 illustrates an ultrasound system 100 for imaging a target region 102 using one or more pulsed ultrasound signals. By way of example, the target region 102 may include one or more biological tissues such as cardiac tissues, liver tissues, breast tissues, prostate tissues, thyroid tissues, lymph nodes, vascular structures and/or other objects suitable for ultrasound imaging. Further, the ultrasound signals may include, for example, one or more reference pulses, one or more pushing pulses and/or one or more tracking pulses.

As used herein, the term "reference pulse" refers to an ultrasonic beam fired at a time when there is little expected motion or a known amount of motion. The reference pulse is typically fired prior to a pushing pulse, or long after a push at a point in time at which the tissue is considered to have returned to a resting or equilibrium position. Particularly, the reference pulse is fired to detect an initial or a reference position of the target region 102. The term "pushing pulse" refers to a high energy ultrasonic beam used to displace the target tissues. Typically, the pushing pulse has a higher transmitting energy than the reference pulse. Further, the term "tracking pulse" describes an ultrasound beam similar to a reference pulse used to detect the position of the target region 102 at a particular instant of time. By way of example, the tracking pulse may be delivered shortly after the delivery of a pushing pulse to determine a displaced position of the target region 102.

Accordingly, in one embodiment, the system 100 includes transmit circuitry 104 that generates a pulsed waveform to drive an array 106 of transducer elements 108, for example piezoelectric crystals within a transducer probe 110, to emit pulsed ultrasonic signals into a body or volume. At least a portion of the pulsed ultrasonic signals back-scatter from the target region 102 to produce echoes that return to the transducer array 106. The transducer elements 108 convert these echo signals into electrical signals and may communicate the electrical signals to receive circuitry 112 for further processing.

In one embodiment, the system 100 further includes a processing unit 114 that controls the operations of the transmit circuitry 104 and the receiver circuitry. To that end, the processing unit 114 includes one or more general-purpose or application-specific processors, digital signal processors, microcomputers, microcontrollers, Application Specific Integrated Circuits (ASICs), Field Programmable Gate Arrays (FPGA) or other suitable devices in communication with other components of the system 100. In certain embodiments, the processing unit 114 operates in response to commands received from a human operator via one or more user input devices 116 such as a keyboard, touchscreen, mouse, buttons and/or switches.

The processing unit 114 provides control and timing signals for controlling the delivery sequence of the different pulses, frequency of delivering the tracking pulses and the pushing pulses, a time delay between two different pulses, beam intensity and/or other imaging system parameters. Particularly, in accordance with aspects of the present technique, the processing unit 114 provides appropriate timing and control signals to the transmit circuitry 104 for delivering a pushing force that induces a shear displacement waveform with a desired wave shape through the target region 102.

To that end, the processing unit 114 divides a pushing pulse having the desired pushing force into shorter segments to generate a plurality of shorter pushing pulse segments. Additionally, the processing unit 114 adapts one or more parameters corresponding to the plurality of shorter pushing pulse segments so as to generate a shear wave that induces desired displacements at a plurality of points along the target region 102. By way of example, the one or more parameters corresponding to the plurality of shorter pushing pulse include amplitude, frequency, pulse length, waveform and/or duty cycle. Particularly, the processing unit 114 determines appropriate values of the one or more parameters for each of the plurality of shorter pushing pulse segments to generate the shear waveform having a desired a sinusoidal, triangular, square, sinc, or coded shape. In one embodiment, the choice of the desired waveforms may be based on the particular algorithm being used for detecting the shift in the shear displacement waveforms and/or a particular statistical form of noise encountered during imaging.

Further, in certain embodiments, the processing unit 114 may store the determined values of the one or more parameters in a memory device 118 for further processing. To that end, the memory device 118 may include storage devices such as a random access memory, a read only memory, a disc drive, solid state memory device and/or a flash memory. Alternatively, the processing unit 114 communicates the determined values to a pulse shaping circuit 120 in the transmit circuitry 104 that generates the plurality of shorter pushing pulse segments. Further, these shorter pushing pulse segments generate a shear displacement waveform having a digital code convolved with a delta function, a multi-level code convolved with a delta function, a sine waveform, a square waveform, a sinc waveform, or combinations thereof. Accordingly, the pulse shaping circuit 120 may include, for example, one or more amplifiers, analog-to digital converters, digital-to-analog converters, filters, a memory and/or a PCI bus interface (not shown). Although, FIG. 1 illustrates the pulse shaping circuit 120 as a part of the transmit circuitry 104, certain embodiments may employ an independent pulse shaping system. Alternatively, the pulse shaping circuit 120 may be provided as a part of another system component such as the processing unit 114 to generate the pulse sequence comprising the plurality of shorter pushing pulse segments having the one or more adapted parameters to generate the shaped waveform.

Inclusion of shaped features into the driving pulse sequence comprising the plurality of shorter pushing pulse segments by varying the one or more parameters results in a shear wave that induces corresponding levels of displacements at different points along the target region 102. Particularly, the resulting displacements approximate the shape and the location of the features included in the driving pulse sequence and convolved with the response of the rest of the system. By way of example, it is known that the pulse length is proportional to the induced displacement. Accordingly, in a sequence of the plurality of shorter pushing pulse segments, if the corresponding pulse lengths are adapted to approximate a sine waveform, the displacements induced by the resulting shear wave also approximate the sine waveform. The resulting displacements determined as a function of time, thus, exhibit the shaped feature, at different locations as the shear wave propagates along the target region 102.

In certain embodiments, the system 100 includes a display device 122, such as a monitor, for displaying an image corresponding to the displacements detected at multiple locations. In one embodiment, the display device 122 may further include a graphical user interface (GUI) for providing a user with configurable options for imaging the target region. By way of example, the configurable options may include a desired wave shape, values of the one or more parameters corresponding to the shorter pushing pulse segments, a selectable region of interest (ROI), a delay profile, a desired pulse sequence and/or other suitable imaging system settings. The configuration options may be adapted to improve the shear wave velocity estimation using shaped pulses for improved correlation detection between the shear displacement waveforms.

Accordingly, the processing unit 114 estimates a correlation between the signals corresponding to the shear displacement waveforms detected at the different locations as a function of time using a timing circuitry (not shown). Particularly, the processing unit 114 uses information corresponding to the location of the shaped feature in the transmitted pulse sequence for quickly estimating the correlation. The processing unit 114 uses the correlated feature to determine a shift between the shear displacement waveform detected at two different target regions. The determined shift may further be used to estimate the velocity of the shear waveform based on the improved correlation. An exemplary method for improving correlation of shear displacement waveforms and estimating the shear wave velocity will be described in greater detail with reference to FIGS. 2-4.

Further, the shear wave velocity depends on material properties of the target region 102. Accordingly, the estimated shear wave velocity may be used to determine tissue mechanical characteristics such as a stiffness or viscosity. The determined tissue characteristics may then be used to identify the presence of a disease or abnormality in the target tissue. An exemplary SWEI method that employs shaped waveforms for improved improving correlation of shear displacement waveforms is described in greater detail with reference to FIG. 2.

Figure 2:
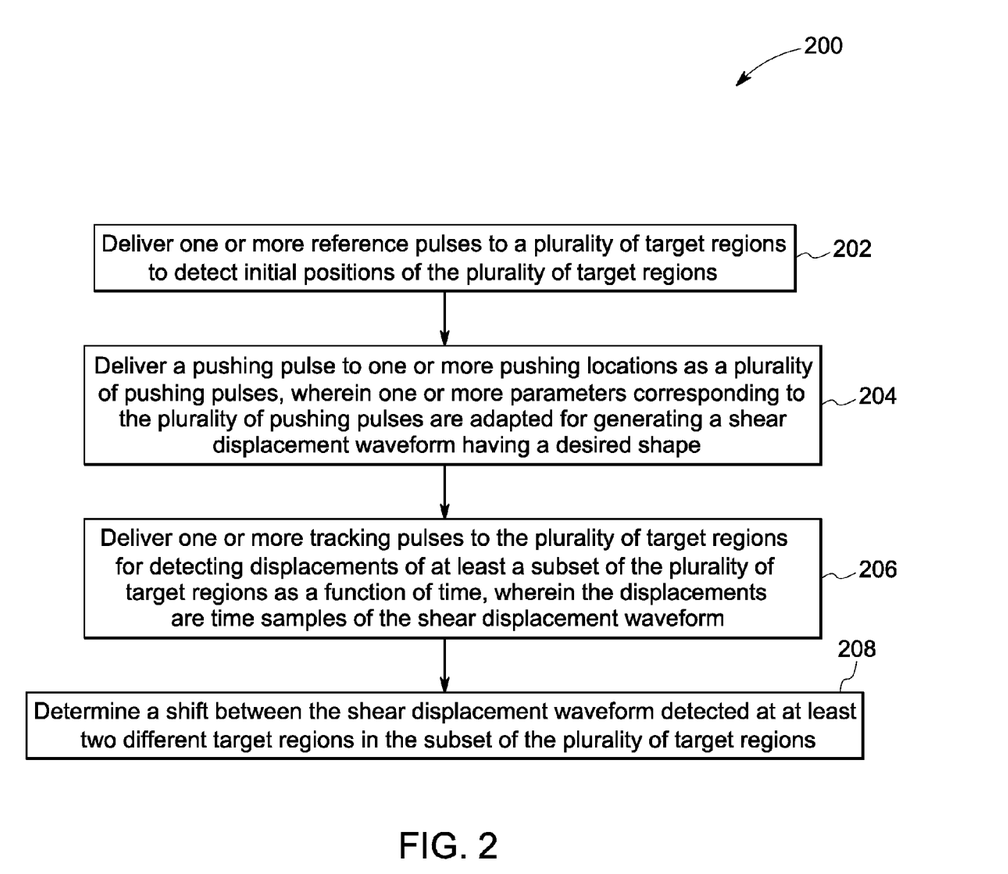
FIG. 2 is a flow diagram depicting an exemplary shear wave elasticity imaging method for improved shear wave velocity estimation, in accordance with aspects of the present technique.

Turning to FIG. 2, a flow chart 200 depicting an exemplary SWEI method, in accordance with certain aspects of the present technique is presented. The exemplary method may be described in a general context of computer executable instructions on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a communication network. In the distributed computing environment, the computer executable instructions may be located in both local and remote computer storage media, including memory storage devices.

Further, in FIG. 2, the exemplary method is illustrated as a collection of blocks in a logical flow chart, which represents operations that may be implemented in hardware, software, or combinations thereof. The various operations are depicted in the blocks to illustrate the functions that are performed generally during different phases of the exemplary SWEI method. In the context of software, the blocks represent computer instructions that, when executed by one or more processing subsystems, perform the recited operations. The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIG. 1.

SWEI is used to differentiate between healthy and diseased tissues based on an estimated velocity of a shear wave as it propagates through the healthy and diseased tissues. Shear wave velocity depends on material properties such as varying tissue density and shear modulus. Accordingly, shear wave elasticity imaging may be used to generate 2D or 3D images for diagnostic and/or prognostic purposes. Typically, during shear wave elasticity imaging, the imaging system focus is set at the target region. By way of example, the target region may include regions that may have increased or decreased stiffness relative to the average surrounding tissue such as tumors, cancerous tissues, ablated tissues and/or hardened blood vessels.

Further, the present description includes embodiments that describe adapting pushing pulse parameters to generate a shear displacement waveform of a desired wave shape to allow for better detection using cross-correlation. Certain embodiments may employ additional methods such as a sum of absolute differences, iterative phase zeroing, cross-correlation and auto-correlation techniques for improving the estimation of the shift between shear displacement waveforms detected at different target regions.

Accordingly, at step 202, transmit circuitry such as the transmit circuitry 104 of FIG. 1 delivers one or more reference pulses to one or more target regions. As previously noted, the reference pulses refer to ultrasonic beams fired at a point in time at which the tissue is considered to be at equilibrium position. The reference pulses, thus, detect an initial or a reference position of each of the one or more target regions. Further, at step 204, the transmit circuitry delivers a pushing pulse to one or more pushing locations to induce a shear wave that propagates through the target regions.

Particularly, the transmit circuitry delivers the pushing pulse as a plurality of shorter pushing pulse segments to a particular push location. To that end, a number N of the shorter pushing pulse segments and one or more corresponding parameters are determined. As previously noted, the one or more parameters may include, for example, amplitude, frequency, phase, pulse length, waveform, and or focus location. Particularly, appropriate values of the one or more parameters for each of the plurality of shorter pushing pulse segments are determined so as to generate the shear displacement waveform having a desired a sinusoidal, triangular, square, sinc, coded or other shape.

Accordingly, a number N and the parameter values are determined such that firing the shorter pushing pulse segments at a specific repetition rate, or at a non-uniform interval, generates a desired displacement as a function of time at the required spatial locations. By way of example, it is known that the pulse length is proportional to induced displacement. Accordingly, the pulse lengths of each of the plurality of shorter pushing pulse segments in a pulse sequence may be adapted to approximate a desired wave shape for the resulting shear displacement waveform.

Figure 3:
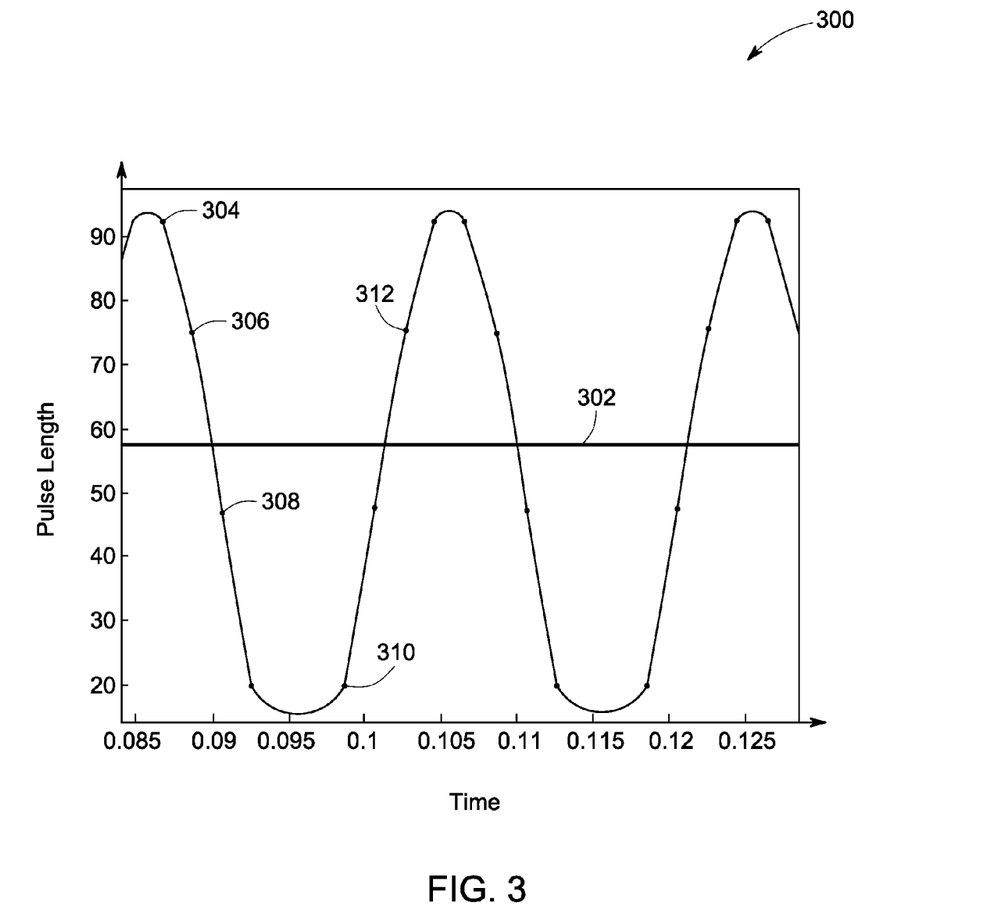
FIG. 3 is a schematic representation of an exemplary pulse sequence used to generate a shear wave that induces varying levels of displacements along a target region using the method of FIG. 2.

By way of example, FIG. 3 illustrates a graphical representation 300 of an exemplary sequence of the plurality of shorter pushing pulse segments having corresponding pulse lengths adapted to approximate a portion of a sine waveform. In FIG. 3, the element 302 is indicative of a plurality of tracking pulses fired at particular instants of time, whereas the circular elements 304, 306, 308, 310 and 312 are indicative of pushing pulse segments applied to a particular push location. Particularly, the Y coordinate position corresponding to a particular pushing pulse segment is indicative of the pulse length used to generate a proper displacement for a particular phase of the sine waveform. Further, the corresponding X coordinate position shows the particular instants of time at which the pushing pulse segment is applied to the push location. By way of example, the pushing pulse segment 304 is fired at a time 87 milliseconds into the exemplary pulse sequence illustrated in FIG. 3. Further, the length of the pushing pulse segment 304 is about 92 microseconds.

As previously noted, the pulse duration or the pulse lengths of the shorter pushing pulse segments are directly proportional to the induced displacement. Accordingly, the pulse length associated with each of the elements 304-328 is varied so as to apply appropriate pushing force to generate a shear displacement waveform that approximates a desired sinusoidal shape. Although, FIG. 3 depicts varying values of pulse lengths, other suitable parameters such as amplitude, frequency, phase, and/or waveform may also be varied to generate a shear displacement waveform corresponding to a desired wave shape. Particularly, appropriate values of the parameters for each of the plurality of shorter pushing pulse segments may be determined so as to generate the shear displacement waveform that causes displacements that approximate, for example, a desired sinusoidal, triangular, square or sinc shape. As previously noted, the choice of the desired waveforms may be based on the particular algorithm being used for determining a shift in the shear displacement waveforms and/or a particular statistical form of noise encountered during imaging.

Returning to step 206 of FIG. 2, one or more tracking pulses are delivered to the plurality of target regions for detecting displacements of the plurality of target regions as a function of time. In the presently contemplated configuration, the tracking pulses are fired after the delivery of the plurality of pushing pulse segments. In alternative embodiments, however, the one or more tracking pulses may be delivered in between the pushing segments for detecting corresponding displacements. Particularly, the tracking pulses are used to determine the displacements of the tissue at least a subset of the through which the shear wave travels. For each target region in the subset, a series of tracking pulses is fired. These tracking pulses are used to determine corresponding displacements for that target region as a function of time. Specifically, for each tracking pulse fired, a corresponding displacement is determined. By way of example, the tracking pulses determine the displacement as of a target region as a function of time using techniques such as speckle tracking techniques, a sum of absolute differences, iterative phase zeroing, direct strain estimators, cross-correlation and auto-correlation techniques.

Figure 4:
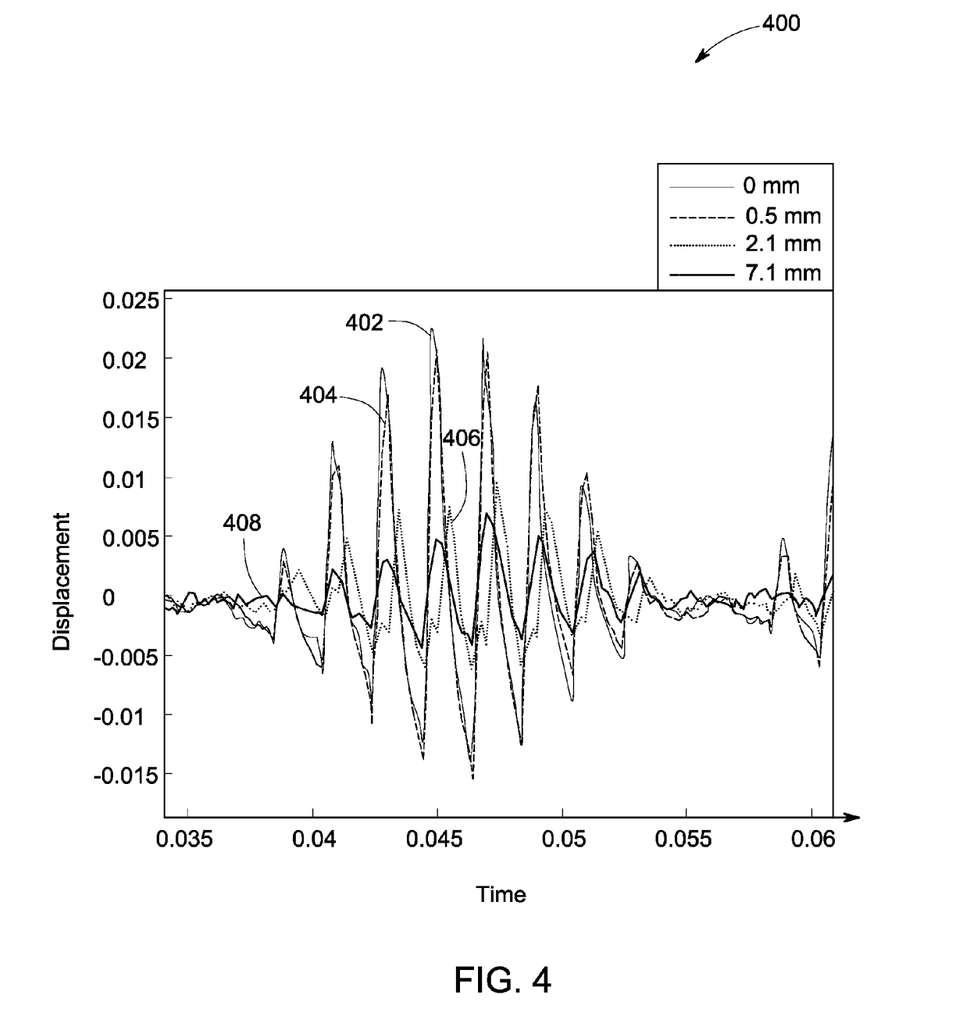
FIG. 4 is a graphical representation of an exemplary configuration of relative displacements of a plurality of locations in a phantom caused by the shear wave generated using the pulse sequence of FIG. 3.

Particularly, FIG. 4 illustrates a graphical representation 400 depicting a plurality of waveforms that are representative of the displacements caused by the delivery of the plurality of shorter pushing pulse segments of FIG. 3 to a particular location in the target tissue. Further, the plurality of shorter pushing pulse segments delivered to the particular locations generate a shear displacement waveform that propagates through the target tissues causing displacement not only at the point of delivery, but also at the plurality of target locations in the target tissues. As previously noted, a series of tracking pulses are used to determine the displacements of the tissue at various locations through which the shear wave travels. In FIG. 4, the waveform 402 is representative of the displacement detected at the point of delivery of the pushing pulse, whereas the waveforms 404, 406 and 408 depict the relative displacements detected at locations that are spatially separated from the point of delivery by 0.5 mm, 2.1 mm and 7.1 mm, respectively. Taken together, each of these displacements detected by the tracking pulses form a shear displacement waveform for a particular tracking location. The shear displacement waveform is sampled at the instant of time at which the tracking pulses were fired. Multiple tracking locations are used, and thus the displacements as function of time are available for each of these locations.

Since the displacements are caused by a traveling shear wave, the shear displacement waveforms for locations that are close together have a similar shape, but are shifted in time. The shift in time is cause by the time it takes for the shear wave to propagate from location to location. Under certain simplifying assumptions, the velocity of the shear wave can be calculated by dividing the distance between at least two different locations by the time shift in the waveform. The time shift can be determined, for example, by cross correlation of the displacement waveforms.

Accordingly, at step 208 of FIG. 2, a shift between the shear displacement waveform detected at least two different target regions in the subset of the plurality of target regions is determined. Particularly, the cross correlation between the shear displacement waveforms detected at least a pair of tracking locations enables determination of the shear wave travel time. As previously described with reference to step 204, the shear displacement waveforms are created with a desired shape and temporal extent. By way of example, FIGS. 3. and 4. depict a 50 Hz sine waveform generated with multiple cycles.

Conventional SWEI techniques typically use a single pushing pulse and cause displacements that generate a single waveform with a single maximum displacement peak. Correlating the single waveform at the plurality of locations is usually difficult owing to the low SNR of the SWEI process, which in turn, affects the accuracy of the shear wave velocity computations. The present SWEI method, however, employs a plurality of shorter pushing pulse segments with adapted pulse parameters to generate a shear displacement waveform with a desired wave shape. By way of example, the sine waveform generated in FIG. 3, by virtue of the multiple cycles and the well-defined wave shape has a higher signal-to-noise ratio (SNR) when correlated in the presence of noise as compared to a simple single push waveform used in conventional SWEI techniques.

The systems and methods disclosed hereinabove describe the use of the pulse shaping technique allows for the inclusion of specific features in the resulting shear displacement waveform to greatly improve the correlation estimation, in turn providing a more accurate estimate of the shear wave velocity. The estimated shear wave velocity values may then be used to generate high resolution ultrasound images that provide greater detail and more accurate levels of information regarding tissue characteristics to aid in a substantially accurate diagnosis.

Accordingly, the present systems and methods may be employed to assess mechanical properties of tissues or any other material that is suitable for shear wave elasticity imaging. By way of example, the systems and methods facilitate characterization of arterial stiffness, assessment of muscle tone and assessment of kidney stiffness for distinguishing between healthy and diseased tissues based on an improved estimate of shear wave velocity through the tissues. Additionally, the exemplary SWEI methods may also be used in radio frequency (RF) ablation therapy such as used for liver cancer to monitor the progress of the therapy in near real-time.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for improving correlation of shear displacement waveforms for ultrasound imaging, comprising:
    delivering one or more reference pulses to a plurality of target regions to detect initial positions of the plurality of target regions;
    delivering a pulse sequence comprising a plurality of pushing pulse segments to one or more pushing locations, wherein one or more parameters corresponding to the plurality of pushing pulse segments are adapted such that the pulse sequence approximates a desired wave shape for generating at least one shear displacement waveform that approximates the same desired wave shape, wherein generating the shear displacement waveform with the desired wave shape comprises generating a sinusoid waveform, a triangular waveform, a square waveform, a sinc waveform, or combinations thereof;
    delivering one or more tracking pulses to the plurality of target regions for detecting displacements of at least a subset of the plurality of target regions as a function of time, wherein the displacements are time samples of the shear displacement waveform;
    determining a shift between the shear displacement waveform detected at least two different target regions in the subset of the plurality of target regions;
    estimating one or more material properties of one or more of the plurality of target regions based on the determined shift; and
    providing control and timing of said reference pulses, pushing pulse segments, and tracking pulses with a processing unit.

2. The method of claim 1, wherein one or more parameters corresponding to the plurality of pushing pulse segments comprise an amplitude, a frequency, a pulse length, a waveform, or combinations thereof.

3. The method of claim 1, wherein generating the shear displacement waveform with the desired wave shape comprises generating a waveform comprising a digital code convolved with a delta function, a multi-level code convolved with a delta function, the sine waveform, the square waveform, the sinc waveform, or combinations thereof.

4. The method of claim 1, wherein determining a shift between the shear displacement waveforms is achieved by a cross-correlation technique, a sum of absolute differences technique, a zero crossing technique, or combinations thereof.

5. The method of claim 1, further comprising estimating a shear velocity based on the determined shift between the shear wave displacement waveform detected at at least the two different target regions.

6. The method of claim 1, further comprising estimating a shear elastic modulus, a viscosity, or a combination thereof, corresponding to the plurality of the target regions based on the determined shift between the shear displacement waveform detected at at least the two different target regions.

7. The method of claim 1, wherein detecting the displacements comprises using speckle tracking, a sum of absolute differences, an iterative phase zeroing technique, a direct strain estimation, a cross-correlation, an auto-correlation, or combinations thereof, for detecting displacements of at least a subset of the plurality of target regions over a determined period of time.

8. The method of claim 1, wherein the target region comprises one or more of a biological tissue and a compressible portion of an object for industrial inspection.

9. An ultrasound system, comprising:
    a transducer array that delivers a pulse sequence comprising a plurality of pulses to a plurality of target regions, wherein the plurality of pulses comprise one or more reference pulses, one or more tracking pulses delivered to the plurality of target regions and at least one pushing pulse delivered to one or more pushing locations as a plurality of pushing pulse segments;
    a pulse shaping unit communicatively coupled to the transducer array, wherein the pulse shaping unit generates at least one shear displacement waveform with a desired wave shape by adapting one or more parameters corresponding to the plurality of pushing pulse segments such that the pulse sequence approximates the desired wave shape; and a processing unit communicatively coupled to at least one of the pulse shaping unit and the transducer array, wherein the processing unit:

adapts the one or more parameters corresponding to the plurality of pushing pulse segments to enable the pulse shaping unit to generate the shear displacement waveform with the desired wave shape;

processes data received from at least a subset of the plurality of target regions in response to the plurality of pushing pulse segments to determine displacements of the plurality of target regions, wherein the displacements are time samples of the shear displacement waveform; and determines a shift between the shear displacement waveform detected at at least two different target regions in the subset of the plurality of target regions.

10. The system of claim 9, further comprising a display device that displays an image corresponding to at least the subset of the plurality of target regions.

11. The system of claim 9, wherein the pulse shaping circuit generates a sinusoidal waveform, a triangular waveform, a square waveform, a sinc waveform, or combinations thereof.

12. The system of claim 9, wherein the pulse shaping circuit generates a waveform having a digital code convolved with a delta function, a multi-level code convolved with a delta function, a sine waveform, a square waveform, a sinc waveform, or combinations thereof.

13. The system of claim 9, wherein the processing unit estimates a shear velocity based on the determined shift between the shear wave displacement waveform detected at least the two different target regions.

14. The system of claim 9, wherein the processing unit estimates a shear elastic modulus, a viscosity, or a combination thereof, corresponding to the plurality of the target regions based on the determined shift between the shear displacement waveform detected at at least the two different target regions.

15. A non-transitory computer readable storage medium with an executable program thereon for improving correlation of shear displacement waveforms, wherein the program instructs a processing unit to perform the following steps:

delivering one or more reference pulses to a plurality of target regions to detect initial positions of the plurality of target regions;

delivering a pulse sequence comprising a plurality of pushing pulse segments to one or more pushing locations, wherein one or more parameters corresponding to the plurality of pushing pulse segments are adapted such that the pulse sequence approximates a desired wave shape for generating at least one shear displacement waveform with the same desired wave shape;

delivering one or more tracking pulses to the one or more target regions for detecting displacements of at least a subset of the plurality of target regions as a function of time, wherein the displacements are time samples of the shear displacement waveform; and determining a shift between the shear displacement waveform detected at least two different target regions in the subset of the plurality of target regions.

16. The non-transitory computer readable storage medium of 15, wherein one or more parameters corresponding to the plurality of pushing pulse segments comprise an amplitude, a frequency, a pulse length, a waveform, or combinations thereof.

17. The non-transitory computer readable storage medium of 15, wherein generating the shear displacement waveform with the desired wave shape comprises generating a sinusoidal waveform, a triangular waveform, a square waveform, a sinc waveform, or combinations thereof.

18. The non-transitory computer readable storage medium of 15, wherein generating the shear displacement waveform with the desired wave shape comprises generating a waveform comprising a digital code convolved with a delta function, a multi-level code convolved with a delta function, a sine waveform, a square waveform, a sinc waveform, or combinations thereof.

19. The non-transitory computer readable storage medium of 15, further comprising estimating a shear velocity a shear elastic modulus corresponding to the plurality of the target regions, a viscosity corresponding to the plurality of the target regions, or combinations thereof, based on the determined shift between the shear wave displacement waveform detected at at least the two different target regions.

* * * * *